United States Patent
Siemer et al.

(10) Patent No.: US 9,096,540 B2
(45) Date of Patent: Aug. 4, 2015

(54) METHOD FOR THE PRODUCTION OF DISUBSTITUTED IMIDAZOLIUM SALTS

(75) Inventors: Michael Siemer, Mannheim (DE); Georg Degen, Lorsch (DE); Peter Groll, Dannstadt-Schauernheim (DE)

(73) Assignee: BASF SE, Ludwigshafen (DE)

( * ) Notice: Subject to any disclaimer, the term of this patent is extended or adjusted under 35 U.S.C. 154(b) by 500 days.

(21) Appl. No.: 12/744,259

(22) PCT Filed: Dec. 8, 2008

(86) PCT No.: PCT/EP2008/067014
§ 371 (c)(1),
(2), (4) Date: May 21, 2010

(87) PCT Pub. No.: WO2009/074535
PCT Pub. Date: Jun. 18, 2009

(65) Prior Publication Data
US 2010/0249432 A1    Sep. 30, 2010

(30) Foreign Application Priority Data
Dec. 12, 2007  (EP) ..................... 07122982

(51) Int. Cl.
*C07D 233/60* (2006.01)
*C07D 233/58* (2006.01)
*C07D 233/00* (2006.01)

(52) U.S. Cl.
CPC ............ *C07D 233/58* (2013.01); *C07D 233/60* (2013.01)

(58) Field of Classification Search
CPC ... C07D 233/60; C07D 233/58; C07D 233/00
USPC ..................................................... 548/335.1
See application file for complete search history.

(56) References Cited

U.S. PATENT DOCUMENTS

| | | | |
|---|---|---|---|
| 5,077,414 A | | 12/1991 | Arduengo, III |
| 5,182,405 A | * | 1/1993 | Arduengo, III ............ 548/335.1 |
| 2008/0269477 A1 | | 10/2008 | Stegmann et al. |

FOREIGN PATENT DOCUMENTS

| | | | |
|---|---|---|---|
| JP | 2004-207451 | * | 7/2004 |
| WO | 91 14678 | | 10/1991 |
| WO | 02 094883 | | 11/2002 |
| WO | 2006 027069 | | 3/2006 |
| WO | 2007 076979 | | 7/2007 |
| WO | 2008 151034 | | 12/2008 |
| WO | 2009 027250 | | 3/2009 |

OTHER PUBLICATIONS

Maginn, Design and Evaluation of Ionic Liquids as Novel CO2 Absorbents, 2005, Quarterly Technical Report, 1-12, University of Notre Dame.*
Pka, 2014, http://www.ochemonline.com/PKa_data.*
Dimethylimidazolium-phosphate, 2014, https://www.spectrumchemical.com/MSDS/TCI-D3240.pdf.*
Vygodskii, S. Yakov et al., "Implementation of ionic liquids as activating media for polycondensation processes", Polymer vol. 45, No. 15, pp. 5031-5045, XP004518193, ISSN: 0032-3861, (Jul. 12, 2004).
Wolfe, M. Derek et al., "Oxidative Desulfurization of Azole-2-thiones with Benzoyl Peroxide: Syntheses of Ionic Liquids and Other Azolium Salts", European Journal of Inorganic Chemistry, No. 17, pp. 2825-2838, XP008111195, ISSN: 1434-1948, (Jun. 6, 2007).
Dzyuba, V. Sergei et al., "New room-temperature ionic liquids with $C_2$-Symmetrical imidazolium cations", Chemical Communication—Chemcom., Royal Society of Chemistry, No. 6, pp. 1466-1467, XP008111201, ISSN: 1359-7345, (Jan. 1, 2001).
U.S. Appl. No. 12/747,372, filed Jun. 10, 2010, Degen, et al.
U.S. Appl. No. 13/511,051, filed May 21, 2012, Neu, et al.

* cited by examiner

*Primary Examiner* — Sun Jae Yoo
(74) *Attorney, Agent, or Firm* — Oblon, McClelland, Maier & Neustadt, L.L.P.

(57) ABSTRACT

Process for preparing 1,3-disubstituted imidazolium salts of the formula I

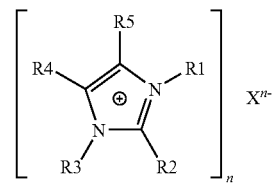

where R1 and R3 are each, independently of one another, an organic radical having from 1 to 20 carbon atoms, R2, R4 and R5 are each, independently of one another, an H atom or an organic radical having from 1 to 20 carbon atoms, X is the anion of a hydrogen acid having a $pK_a$ of at least 2 (measured at 25° C., 1 bar in water or dimethyl sulfoxide) and n is 1, 2 or 3, wherein a) an α-dicarbonyl compound, an aldehyde, an amine and the hydrogen acid of the anion X⁻ are reacted with one another and b) the reaction is carried out in water, a solvent which is miscible with water or a mixture thereof.

25 Claims, No Drawings

METHOD FOR THE PRODUCTION OF DISUBSTITUTED IMIDAZOLIUM SALTS

The invention relates to a process for preparing 1,3-disubstituted imidazolium salts of the formula I

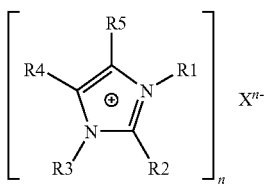

where
R1 and R3 are each, independently of one another, an organic radical having from 1 to 20 carbon atoms,
R2, R4 and R5 are each, independently of one another, an H atom or an organic radical having from 1 to 20 carbon atoms,
X is the anion of a hydrogen acid having a $pK_a$ of at least 2 (measured at 25° C., 1 bar in water or dimethyl sulfoxide) and
n is 1, 2 or 3,
wherein
a) an α-dicarbonyl compound, an aldehyde, an amine and the hydrogen acid of the anion X⁻ are reacted with one another and
b) the reaction is carried out in water, a solvent which is miscible with water or a mixture thereof.

Imidazolium salts have great importance as ionic liquids. For the purposes of the present invention, ionic liquids are salts having a melting point of less than 200° C., in particular salts which are liquid at room temperature.

Ionic liquids, in particular imidazolium salts, are suitable, for example, as solvents in many industrial applications, e.g. for the dissolution of cellulose.

Very simple and inexpensive processes for preparing such imidazolium salts in very high purity and quality are therefore desirable.

WO 91/14678 describes a single-stage process for preparing imidazolium salts from an α-dicarbonyl compound, an aldehyde, an amine and an acid. Water is removed by azeotropic distillation using toluene as entrainer. The process described is a batch process; a continuous process involving an azeotropic distillation is generally not possible.

Undesirable by-products, in particular the ammonium salt of the acid used, are obtained in this reaction. Preferred acids are strong acids having a $pK_a$ of less than 4. Furthermore, the reaction is carried out in an organic solvent. The organic solvent and the water formed in the reaction have to be removed in a complicated fashion by azeotropic distillation. Owing to other by-products, the reaction product obtained has a dark to black color.

A similar process is known from WO 02/94883. Here, hydrophobic, e.g. fluorinated, anions are used so that the products form a separate phase and can easily be separated off from the aqueous phase. The process described here is also a batch process.

The single-stage processes known hitherto for preparing imidazolium salts therefore do not yet meet the above requirements to a satisfactory extent.

It is therefore an object of the present invention to provide a process for preparing imidazolium salts, which is very simple to carry out and therefore inexpensive and gives reaction products in high yield and quality.

We have accordingly found the process defined at the outset.

Imidazolium Salts

According to the invention, 1,3-disubstituted imidazolium salts of the formula I

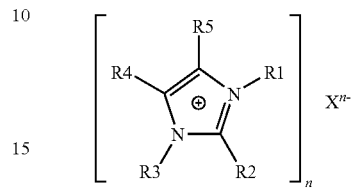

where
R1 and R3 are each, independently of one another, an organic radical having from 1 to 20 carbon atoms,
R2, R4 and R5 are each, independently of one another, an H atom or an organic radical having from 1 to 20 carbon atoms,
X is the anion of a hydrogen acid having a $pK_a$ of at least 2 (measured at 25° C., 1 bar in water or dimethyl sulfoxide) and
n is 1, 2 or 3, are prepared.

Preference is given to R1 and R3 each being, independently of one another, an organic radical having from 1 to 10 carbon atoms. The organic radical can also comprise further heteoatoms, in particular oxygen atoms, for example hydroxyl groups, ether groups, ester groups or carbonyl groups.

In particular, R1 and R3 are each a hydrocarbon radical which can comprise hydroxyl groups, ether groups, ester groups or carbonyl groups in addition to carbon and hydrogen.

Particular preference is given to R1 and R3 each being, independently of one another, a hydrocarbon radical which has from 1 to 20 carbon atoms, in particular from 1 to 10 carbon atoms, and comprises no other heteroatoms, e.g. oxygen or nitrogen. The hydrocarbon radical can be aliphatic (which also includes unsaturated aliphatic groups) or aromatic or comprise both aromatic and aliphatic groups. Preference is given to R1 and R2 being an aliphatic hydrocarbon radical.

Possible hydrocarbon radicals are, for example, the phenyl group, benzyl group, a phenyl group or benzyl group substituted by one or more C1-C4-alkyl groups, alkyl groups and alkenyl groups, in particular the allyl group.

Very particular preference is given to R1 and R3 each being a C1-C10-alkyl group. As alkyl group, particular preference is given to a C1-C6-alkyl group, and in a particular embodiment the alkyl group is a C1-C4-alkyl group.

Very particular preference is given to R1 and R3 each being, independently of one another, a methyl, ethyl, n-propyl, isopropyl, n-butyl, sec-butyl or tert-butyl group, with the methyl, ethyl, n-propyl and n-butyl groups being of particular importance.

In a preferred embodiment, R1 and R3 are each the same organic radical; the imidazolium salts of the formula I are therefore particularly preferably symmetrical, disubstituted imidazolium salts.

In a likewise preferred embodiment, the imidazolium salts are mixtures of imidazolium salts of the formula I having different radicals R1 and R3. Such mixtures can be obtained by use of different amines, e.g. primary amines having different alkyl groups. The mixture obtained then comprises both imidazolium salts in which R1 and R3 are identical and imidazoliuim salts in which R1 and R3 have different meanings.

In a particular embodiment:
R1 and R3 are each a methyl group,
R1 and R3 are each an ethyl group,
R1 and R3 are each an n-propyl group,
R1 and R3 are each an n-butyl group,
R1 is a methyl group and R3 is an ethyl group,
R1 is a methyl group and R3 is an n-propyl group,
R1 is a methyl group and R3 is an n-butyl group,
R1 is a methyl group and R3 is an allyl group,
R1 is an ethyl group and R3 is an allyl group,
R1 is a methyl group and R3 is a benzyl group,
R1 is an ethyl group and R3 is a benzyl group.

R2, R4 and R5 are each, independently of one another, an H atom or an organic radical having from 1 to 20 carbon atoms, with R4 and R5 together also being able to form an aliphatic or aromatic ring. The organic radical can also comprise heteroatoms such as nitrogen or oxygen in addition to carbon and hydrogen; it can preferably comprise oxygen, in particular in the form of hydroxyl groups, ester groups, ether groups or carbonyl groups.

In particularly, R2, R4 and R5 are each, independently of one another, an H atom or a hydrocarbon radical which can also comprise at most hydroxyl groups, ether groups, ester groups or carbonyl groups in addition to carbon and hydrogen.

Preference is given to R2, R4 and R5 each being, independently of one another, a hydrogen atom or a hydrocarbon radical which has from 1 to 20 carbon atoms, in particular from 1 to 10 carbon atoms, and comprises no other heteroatoms, e.g. oxygen or nitrogen. The hydrocarbon radical can be aliphatic (which also includes unsaturated aliphatic groups) or aromatic or comprise both aromatic and aliphatic groups, with R4 and R5 also being able to form an aromatic or aliphatic hydrocarbon ring which may optionally be substituted by further aromatic or aliphatic hydrocarbon groups (the number of carbon atoms of the optionally substituted hydrocarbon ring including the substituents can preferably be a maximum of 40, in particular a maximum of 20, particularly preferably a maximum of 15 or a maximum of 10).

As hydrocarbon radicals, mention may be made of, for example, the phenyl group, the benzyl group, a phenyl group or benzyl group substituted by one or more C1-C4-alkyl groups, alkyl groups, alkenyl groups and, when R4 and R5 form a ring, an aromatic 5-or 6-membered ring formed by R4 and R5, a cyclohexene or cyclopentene ring, with these ring systems being able, in particular, to be substituted by one or more C1-C10 alkyl groups, in particular C1-C4-alkyl groups.

Aliphatic hydrocarbon radicals are preferred as hydrocarbon radicals.

Particular preference is given to R2, R4 and R5 each being, independently of one another, an H atom, a C1-C8-alkyl group or a C1-C8-alkenyl group, e.g. an allyl group.

Very particular preference is given to R2, R4 and R5 each being, independently of one another, an H atom, a methyl, ethyl, n-propyl, isopropyl, n-butyl, sec-butyl or tert-butyl group, with the methyl, ethyl, n-propyl and n-butyl groups being of particular importance.

In a particular embodiment, R2 is, independently of the other radicals R4 and R5 and the other radicals R1 and R3, an H atom. Imidazolium salts of the formula I in which R2 is an H atom are particularly advantageous for the purposes of the present invention: they have good solubility in epoxy compounds and are very effective as latent catalyst. In a particular embodiment, R2 is an H atom when the anion is an acetate.

In a particular embodiment,
R2, R4 and R5 are each an H atom,
R2 is an H atom or a C1-C4-alkyl group and R4, R5 are each an H atom or a C1-C4-alkyl group.

As individual cases of the cations of the compounds of the formula I, mention may be made of:
1-butyl-3-methylimidazolium (R1=butyl, R3=methyl)
1-butyl-3-ethylimidazolium (R1=butyl, R3=ethyl)
1,3-dimethylimidazolium (R1=methyl, R3=methyl)
1-ethyl-3-methylimidazolium (R1=ethyl, R3=methyl)
1-ethyl-2,3 dimethylimidazolium (R1=ethyl, R2=methyl, R3=methyl)

In formula I, n is 1, 2 or 3; the anion accordingly has one, two or three negative charges and one, two or three imidazolium cations are accordingly present in the salt.

n is preferably 1 or 2, particularly preferably 1; the anion is therefore particularly preferably monovalent.

In formula I, X is the anion of a hydrogen acid having a $pK_a$ of at least 2, in particular at least 3 and in a particular embodiment at least 4 (measured at 25° C., 1 bar in water or dimethyl sulfoxide).

The $pK_a$ of the hydrogen acid of the anion X is preferably from 2 to 15, preferably from 3 to 15, in particular from 3 to 8 and particularly preferably from 4 to 6.

The $pk_a$ is the logarithm to the base 10 of the acidity constant $K_a$. The $pK_a$ is for this purpose measured at 25° C., 1 bar, either in water or dimethyl sulfoxide as solvent; according to the invention, it is therefore sufficient for an anion to have the appropriate $pK_a$ either in water or in dimethyl sulfoxide. Dimethyl sulfoxide is used particularly when the anion is not readily soluble in water. Literature data for the two solvents may be found in standard textbooks.

Suitable anions X⁻ are, in particular, compounds having one or more carboxylate groups (carboxylates for short) which have the above $pk_a$.

As such carboxylates, mention may be made of, in particular, organic compounds which have from 1 to 20 carbon atoms and comprise one or two carboxylate groups, preferably one carboxylate group.

The carboxylates can be either aliphatic or aromatic compounds. For the present purposes, aromatic compounds are compounds comprising aromatic groups. Particular preference is given to aliphatic or aromatic compounds which comprise no further heteroatoms apart from the oxygen atoms of the carboxylate group or comprise at most one or two hydroxyl groups, carbonyl groups or ether groups. Very particular preference is given to aliphatic or aromatic compounds which comprise no further heteroatoms apart from the oxygen atoms of the carboxylate group.

As compounds having two carboxylate groups, mention may be made of, for example, the anions of phthalic acid, of isophthalic acid, of C2-C6-dicarboxylic acids, e.g. oxalic acid, malonic acid, succinic acid, glutaric acid, adipic acid.

As compounds having one carboxylate group, mention may be made of the anions of aromatic, aliphatic, saturated or unsaturated C1-C20-carboxylic acids, in particular alkanecarboxylic acids, alkenecarboxylic acids, alkynecarboxylic acids, alkadienecarboxylic acids, alkatrienecarboxylic acids, hydroxycarboxylic acids or ketocarboxylic acids or aromatic carboxylic acids such as benzoic acid or phenylacetic acid. Suitable alkanecarboxylic acids, alkenecarboxylic acids and alkadienecarboxylic acids are also known as fatty acids.

As anions X, mention may be made of, in particular, the benzoate anion and the anions of C1-C20-alkanecarboxylic acids which may optionally be substituted by one or two hydroxy groups, preferably one hydroxy group. Particular preference is given to the benzoate anion and the anions of C2-C20-alkanecarboxylic acids; in particular the acetate anion and propionate anion; very particularly preferably the acetate anion. Preferred imidazolium salts of the formula I are soluble in water or miscible with water. In particular, the solubility in water or miscibility with water is at least 50 grams of imidazolium salt, particularly preferably at least 100 grams of imidazolium salt, very particularly preferably at least 200 grams of imidazolium salt and in particular at least 300 grams of imidazolium salt, per 1 liter of water (at 1 bar, 21° C.).

As imidazolium salts, mention may be made of, in particular, 1,3-disubstituted imidazolium salts of the formula I in which
R1 and R3 are identical
and
X is a compound having a carboxylate group,
and particularly preferably
1,3-disubstituted imidazolium salts of the formula I in which
R1 and R3 are identical and are each a $C_2$-$C_4$-alkyl group, in particular an ethyl group,
R2, R4 and R5 are each an H atom
and X is an acetate anion or a propionate anion.

Starting Compounds for the Preparation

According to the invention, an α-dicarbonyl compound, an aldehyde, an amine and a hydrogen acid of the anion $X^-$ are reacted with one another.

The above starting compounds are selected according to the desired radicals R1 to R5 in formula I.

The α-dicarbonyl compound is preferably a compound of the formula II

R4—CO—CO—R5, where R4 and R5 are as defined above.

Particular preference is given to glyoxal.

The aldehyde is, in particular, an aldehyde of the formula R2-CHO, where R2 is as defined above. Particular preference is given to formaldehyde; the formaldehyde can also be used in the form of formaldehyde-liberating compounds such as paraformaldehyde or trioxane.

The amines are, in particular, primary amines of the type R—NH2. The radical R corresponds to the radicals R1 and R3 of the imidazolium salts obtained. If one defined primary amine is used, an imidazolium salt in which the radicals R1 and R3 are identical is obtained. If a mixture of amines (e.g. mixture of R'—NH2 and R"—NH2) is used, a mixture of imidazolium salts (mixture of salts in which R1 and R3=R', R1 and R3=R" and salts in which R1=R' and R3=R" is obtained).

The hydrogen acid is the desired hydrogen acid of the anion X, preferably an alkanecarboxylic acid, particularly preferably acetic acid.

Way of Carrying Out the Process

According to the invention, the reaction of the starting compounds is carried out in water, a solvent which is miscible with water or a mixture thereof.

As solvents which are miscible with water, mention may be made of, in particular, protic solvents, preferably aliphatic alcohols or ethers having a maximum of 4 carbon atoms, e.g. methanol, ethanol, methyl ethyl ether, tetrahydrofuran. Suitable protic solvents are miscible in any ratio with water (at 1 bar, 21° C.).

The reaction is preferably carried out in water or mixtures of water with the above protic solvents. The reaction is particularly preferably carried out in water.

The removal of the water or solvent after the reaction is preferably carried out without using hydrophobic organic solvents which are not miscible with water (hydrocarbons, e.g. toluene) as entrainers.

The reaction mixture particularly preferably does not contain any hydrophobic organic solvents which are immiscible with water, e.g. hydrocarbons, either during or after the reaction; in particular, the reaction mixture does not comprise any solvents other than water or the protic solvents mentioned (either during or after the reaction).

The reaction of the starting components can be carried out at atmospheric pressure and, for example, temperatures of from 5 to 100° C., in particular from 5 to 50° C., particularly preferably from 10 to 40° C.

The starting components can be combined in any order.

The reaction can be carried out batchwise, semicontinuously or continuously. In the semicontinuous mode of operation, it is possible, for example, to place at least one starting compound in a reaction vessel and feed in the remaining starting components.

In the continuous mode of operation, the starting components are combined continuously and the product mixture is discharged continuously. The starting components can be introduced individually or as a mixture of all or part of the starting components. In a particular embodiment, the amine and the acid are mixed beforehand and fed in as one stream, while the other components can be fed in individually or likewise as a mixture (2nd stream).

In a further particular embodiment, all starting components comprising carbonyl groups (i.e. the α-dicarbonyl compound, the aldehyde and the hydrogen acid of the anion X if this is a carboxylate) are mixed beforehand and fed in jointly as one stream; the remaining amine is then introduced separately.

The continuous preparation can be carried out in any reaction vessels, e.g. a stirred vessel. Preference is given to carrying it out in a cascade of stirred vessels, e.g. from 2 to 4 stirred vessels, or in a tube reactor.

The reaction mixture obtained is generally dark in color because of by-products. A lightening of the color of the reaction mixture can in the present case surprisingly be achieved by means of oxidation.

For this purpose, the reaction mixture obtained can be treated with an oxidant. The oxidant can be, for example, gaseous or liquid. A particularly useful oxidant is gaseous oxygen which is brought into contact with the reaction mixture in a suitable way, e.g. by means of pressure and/or introduction beneath the surface of the liquid.

Further suitable oxidants are, in particular, liquid oxidants, in particular oxidants which are dissolved in suitable solvents which are miscible with the reaction mixture. Particularly useful solvents are water, solvents which are miscible with water and mixtures thereof.

As solvents which are miscible with water, particular mention may be made of protic solvents, preferably aliphatic alcohols or ethers having a maximum of 4 carbon atoms, e.g. methanol, ethanol, methyl ethyl ether, tetrahydrofuran. Suitable protic solvents are miscible in any ratio with water (at 1 bar, 21° C.).

The oxidant is preferably present in solution in water or a mixture of water with the above protic solvents; it is particularly preferably present as a solution in water.

Suitable oxidants are known to those skilled in the art. Oxidants are compounds having a high electron affinity (electrophilicity). Strongly electrophilic compounds which are therefore suitable as oxidant are, for example, oxygen and oxygen-comprising per compounds, in particular hydrogen peroxide, metal peroxides or organic peroxides, e.g. sodium persulfate or tert-butyl hydroperoxide, inorganic and organic peracids, e.g. periodic acid or percarboxylic acids, and also other compounds such as sulfur or metal compounds in high oxidation states (e.g. iron(III) compounds, manganese dioxide, potassium permanganate, chromic acid, chromic anhydride, lead dioxide or lead tetraacetate).

Preference is given to gaseous oxygen and in particular hydrogen peroxide, preferably in the form of solutions as above, in particular as from 10 to 40% strength by weight solution.

The amount of oxidant is selected according to requirements; per 1 mol of imidazolium salt (on the basis of the amount theoretically obtained from the reaction mixture), it is possible to use, for example, from 0.1 to 20 mol, preferably from 0.5 to 10 mol, of oxidant.

The oxidation can, for example, be carried out at temperatures of from 20 to 100° C., in particular from 50 to 90° C., under atmospheric pressure until the color of the mixture becomes lighter.

Water and/or other solvent (see above), preferably water, is preferably distilled off directly from the reaction mixture, i.e. no entrainer (e.g. an organic solvent which is not miscible with water, is used.

The water and/or other solvent can be separated off before or after the above-described oxidation. If an oxidation is carried out, the water is preferably separated off afterwards.

Excess acid (HX) is preferably neutralized, e.g. by means of alkali metal hydroxide, in particular sodium hydroxide. The salt formed (NaX) can preferably be precipitated by addition of a suitable solvent such as acetonitrile or methanol and be removed from the mixture. The solvent used can then be separated off again, e.g. by distillation.

In the process of the invention, imidazolium salts are obtained in high purity and yield by means of an only single-stage reaction. The measures for the reaction and work-up are simple to carry out. Undesirable salts such as ammonium salts which can be removed only with difficulty are not obtained in the process of the invention. Excess acid can easily be removed. In particular, the process can also be carried out continuously.

EXAMPLES

1. Example

Preparation of 1,3-diethylimidazolium acetate (EEIM acetate)

Reaction Equation:

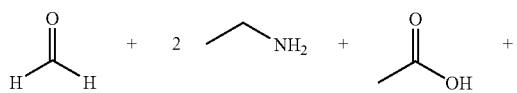

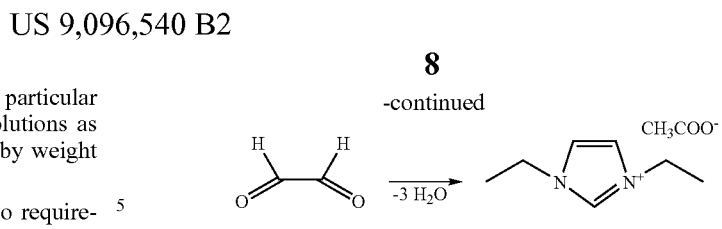

Stirring speeds: Reaction vessel: 350 rpm
Apparatus: 6 l four-neck flask, Teflon half-disk stirrer, thermometer, condenser, dropping funnel
Batch:

| Substance |
|---|
| 252.1 g 8.15 mol of paraformaldehyde 97% strength and 325 g 18.04 mol of water placed in a reaction vessel |
| 1048.7 g 16.27 mol of ethylamine 70% strength in water added dropwise |
| 488.9 g 8.15 mol of glacial acetic acid added dropwise |
| 1181.4 g 8.15 mol of glyoxal 40% strength in water added dropwise |

| Time | Temperature | |
|---|---|---|
| 8:55 | 10° C. | Paraformaldehyde and water placed in a reaction vessel, white suspension, ethylamine added dropwise at 20-30° C., exothermic reaction, cooling in an ice bath |
| 9:35 | 23° C. | After half of the amine has been added, the exothermic reaction abates and a clear solution is formed |
| 9:50 | 23° C. | End of addition, mixture stirred for another 30 min at RT |
| 10:35 | 25° C. | Glacial acetic acid added dropwise at 20-30° C., exothermic reaction, cooling in an ice bath, white mist formed |
| 11:10 | 25° C. | End of addition, two clear phases, mixture stirred for a further 20 min at RT |
| 11:30 | 21° C. | Glyoxal added dropwise at 20-35° C., the mixture becomes a single phase and changes color from yellow to blackish brown |
| 12:00 | 22° C. | End of addition, mixture stirred overnight at RT |

Work-up:

The blackish brown product mixture obtained was heated to 70° C. (pH 6.68) and 1.5 kg of hydrogen peroxide 30% strength were added dropwise at 70-80° C. over a period of about 1 hour. After the addition was complete, a lightening of the color was observed (pH 6.33). The mixture was stirred for another 4 hours at 80° C. (no gas evolution), resulting in a further lightening of the color (light orange, (pH 6.08)).

The stirring speed was increased to 480 rpm and about 375 g of NaOH 40% strength was added dropwise over about 1.5 hours to neutralize excess acid. The temperature stayed at 65° C. without further heating, and the pH increases to 9.5 with very vigorous evolution of gas (decomposition of hydrogen peroxide, $H_2O_2$). The temperature rose to 95° C. at pH 10.3. The addition was stopped and the mixture was stirred overnight at room temperature (RT) (lightening of the color to yellow).

The product mixture (pH 11.2) was evaporated on a rotary evaporator, 1.5 kg of acetonitrile were added and the mixture was stirred overnight. The sodium salt of the excess acid precipitates and is separated off. The mixture was then evaporated on a rotary evaporator.

A total of 1444.14 grams of product (EEIM acetate, 1H-NMR) were obtained.

TABLE 1 with examples 2 to 11

| Example No. | Starting material 1 | Further starting materials | Work-up and procedure | Product (determined by (1H NMR) |
|---|---|---|---|---|
| 2 | <br>1 eq (70% strength in H₂O)<br><br>1 eq (40% strength in H₂O) | <br>1 eq (97% strength)<br><br>1 eq (40% strength in H₂O)<br><br>1 eq<br>pK$_a$ = : 4.75 | 1 eq of ethylamine added dropwise to a suspension comprising 1 eq of paraformaldehyde in H₂O at <31° C. (exothermic reaction, ice bath). Mixture stirred further for about 30 minutes. Mixture cooled to about 3° C. by means of an ice bath and 1 eq of methylamine run in at 3-5° C.<br>1 eq of glacial acetic acid added dropwise at <20° C. (exothermic reaction, ice bath), 2-phase mixture<br>1 eq of glyoxal solution added (exothermic reaction, ice bath, homogeneous) and mixture stirred at RT for 5 days. Mixture evaporated to dryness on a rotary evaporator (black-brown oil) | 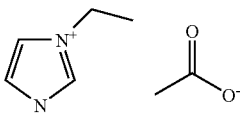<br>Mixture of products<br>MMIM* acetate/EEIM* acetate/EMIM* Acetate<br>1:1.25:2.13 |
| 3 | <br>2 eq (70% strength in H₂O) | <br>1 eq (97% strength)<br><br>1 eq (40% strength in H₂O)<br><br>1 eq<br>pK$_a$ 3.0 | 1 eq of ethylamine added dropwise to a suspension comprising 1 eq of paraformaldehyde in H₂O at <31° C. (exothermic reaction, ice bath). Mixture stirred further for about 30 minutes. Cooled to about 3° C. by means of ice bath and 1 eq of methylamine run in at 3-5° C.<br>1 eq of glycolic acid added dropwise at <20° C (exothermic reaction, ice bath), 2-phase mixture.<br>1 eq of glyoxal solution added (exothermic reaction, ice bath, homogeneous) and mixture stirred at RT for 5 days. Mixture evaporated to dryness on a rotary evaporator (black-brown oil) | 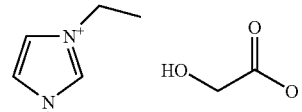 |

TABLE 1-continued with examples 2 to 11

| Example No. | Starting material 1 | Further starting materials | Work-up and procedure | Product (determined by (1H NMR) |
|---|---|---|---|---|
| 4 |  2 eq | 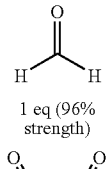 1 eq (96% strength) <br><br> 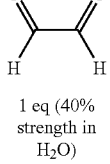 1 eq (40% strength in H$_2$O) <br><br> 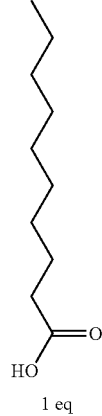 1 eq | ED1 added dropwise to a suspension comprising 1 eq of paraformaldehyde in toluene at 20-30° C. (slightly exothermic reaction, cooling in an ice bath). Mixture stirred further at RT for 10 minutes, turbid 1 eq of decanoic acid dissolved in toluene added dropwise at 20-30° C. over a period of about 20 minutes (slightly exothermic reaction, cooling in an ice bath, slightly foamy). Mixture stirred further for about 30 minutes. 1 eq of glyoxal solution added dropwise to the milky suspension at 20-30° C. over a period of about 4 hours (85-110° C. Internal temperature). Mixture evaporated to dryness on a rotary evaporator (black-brown oil) | 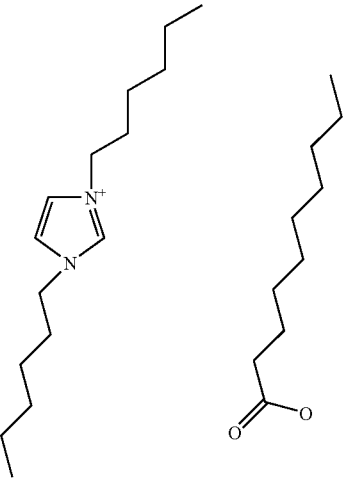 [SMILES: CCCCCCn1cc[n+](CCCCCC)c1 ; CCCCCCCCCC(=O)O] |
| 5 |  2 eq | 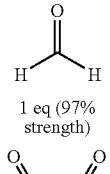 1 eq (97% strength) <br><br> 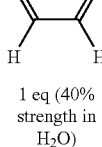 1 eq (40% strength in H$_2$O) <br><br> 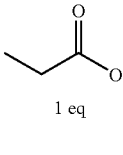 1 eq | 2 eq of ED1 added dropwise to a suspension comprising 1 eq of paraformaldehyde in H$_2$O at 20-30° C. (exothermic reaction, ice bath). Mixture stirred further for about 10 minutes. 1 eq of propionic acd added dropwise at 20-30° C. (exothermic reaction, ice bath, 2-phase mixture, yellow-orange turbid suspensions, stirred further for about 30 minutes. 1 eq of glyoxal solution added dropwise at 20-30° C. (exothermic reaction, ice bath) and stirred overnight at RT (water cooling). The reddish, heterogeneous mixture evaporated at max 70° C./4 mbar on a rotary evaporator (reddish brown oil) pH (10% strength solution in EtOH/H$_2$O 4:1 of R1) = 6.50, H$_2$O nKF = 1.2050% Product dissolved in acetonitrile and admixed with 1M KOH/EtOH, stirred at RT for about 2 hours, solid filtered off with suction, K1. Filtrate evaporated (oil, comprises solid) pH (10% strength solution in EtOH/H$_2$O 4:1 of R1) = 8.40 again stirred overnight in acetonitrile at RT, solid filtered off with suction, filtrate evaporated (reddish brown oil) | 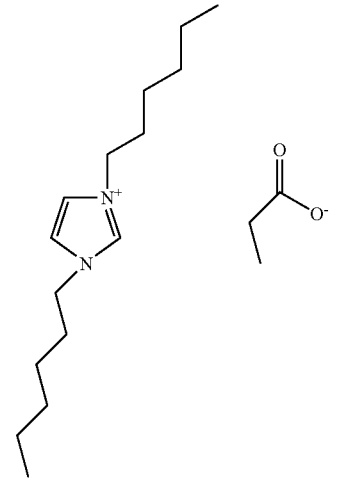 |

TABLE 1-continued with examples 2 to 11

| Example No. | Starting material 1 | Further starting materials | Work-up and procedure | Product (determined by (1H NMR)) |
|---|---|---|---|---|
| 6 |  NH$_2$, 2 eq | 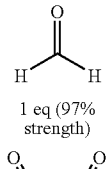 formaldehyde 1 eq (97% strength); glyoxal 1 eq (40% strength in H$_2$O); benzoic acid 1 eq | 2 eq of ED1 added dropwise to a suspension comprising 1 eq of paraformaldehyde in H$_2$O at 20-30° C. (exothermic reaction, ice bath). Mixture stirred further for about 10 minutes. 1 eq of benzoic acid added a little at a time by means of a spatula at 20-30° C. (exothermic reaction, ice bath, yellow clear suspension), mixture stirred further for about 30 minutes. 1 eq of glyoxal solution added dropwise at 20-30° C. (exothermic reaction, ice bath) and mixture stirred overnight at RT (water cooling). The heterogeneous mixture transferred to a single-neck flask and evaporated at max. 70° C./4 mbar on a rotary evaporator, R1 (reddish brown oil which crystallizes through). A yellowish solid remains adhering to the wall in the reaction flask; this is transferred by means of toluene into a single-neck flask and evaporated at max. 70° C./4 mbar, R2. R1 and R2 combined (R3) R3 dissolved in EtOH/acetonitrile and admixed with 1M KOH/EtOH, stirred at RT for about 1 hour, solid filtered off with suction, K1. Filtrate evaporated, R40 solid) pH (10% strength solution in EtOH/H$_2$O 4:1 of R4) = 8.01 R4 again stirred overnight in acetonitrile at room temperature (RT)T, solid filtered off with suction, filtrate evaorated, R5 (reddish brown solid) | 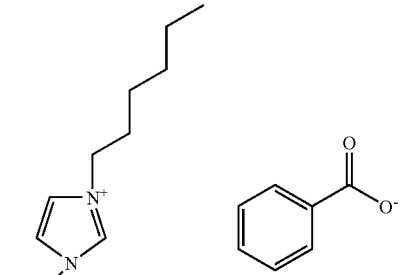 |
| 7 |  NH$_2$, 2 eq | 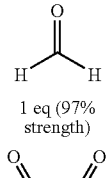 formaldehyde 1 eq (97% strength); glyoxal 1 eq (40% strength in H$_2$O); propionic acid 1 eq | 2 eq of ED1 added dropwise to a suspension comprising 1 eq of paraformaldehyde in H$_2$O at 20-30° C. (exothermic reaction, ice bath). Mixture stirred further for about 10 minutes. 1 eq of propionic acid added dropwise at 20-30° C. (exothermic reaction, ice bath), mixture stirred further for about 30 minutes. 1 eq of glyoxal solution added dropwise at 20-30° C. (exothermic reaction, ice bath) and stirred overnight at RT (water cooling). The heterogeneous mixture evaporated at max 70° C./4 mbar on a rotary evaporator, R1 (dark brown oil) R1 dissolved in acetonitrile and admixed with 1M KOH/EtOH, stirred at RT for about 2 hours, solid filtered off with suction, K1. Filtrate evaporated, R2 (oil, comprises solid) R2 again stirred in acetonitrile at RT for 5 hours, solid filtered off with suction, filtrate evaporated, R3 (reddish brown oil) | 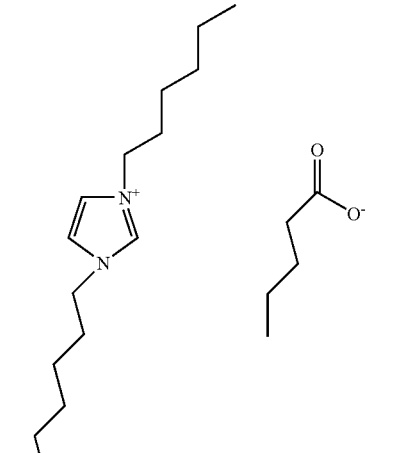 |

TABLE 1-continued with examples 2 to 11

| Example No. | Starting material 1 | Further starting materials | Work-up and procedure | Product (determined by (1H NMR) |
|---|---|---|---|---|
| 8 | 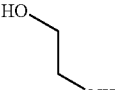<br>2 eq | <br>1 eq (36.5% strength in H₂O)<br><br>1 eq (40% strength in H₂O)<br><br>1 eq | 2 eq of ED1 added dropwise to a solution comprising 1 eq of formalin, 1 eq of glyoxal solution and 1 eq of Ch3COOH at <40° C. (exothermic reaction, cooling in an ice bath). Mixture stirred at RT over the weekend. The light-brown solution changes into a dark-brown solution. Mixture evaporated at max 70° C./4 mbar on a rotary evaporator, R1 (blackish-brown oil) |  |
| 9 | 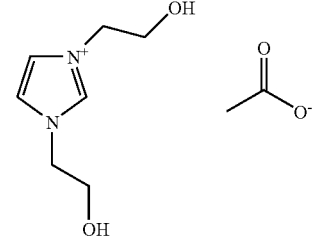<br>1 eq (70% strength in H₂O)<br><br>1 eq (40% strength in H₂O) | <br>1 eq (36.5% strength in H₂O)<br><br>1 eq (40% strength in H₂O)<br><br>1 eq | 1 eq of glyoxal solution and 1 eq of formalin and 1 eq of glacial acetic acid are placed in a reaction vessel (slightly exothermic reaction), homogeneous. 1 eq of ethylamine + 1 eq of methylamine added dropwise at <35° C. (exothermic reaction, cooling in an ice bath). The solution stirred overnight at RT. The dark brown solution evaporated on a rotary evaporator, R1 (blackish brown oil) | <br><br><br>MMIM* acetate/EEIM* acetate<br>25:25:50 |
| 10 | 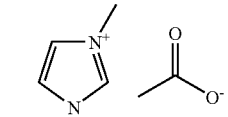<br>2 eq | 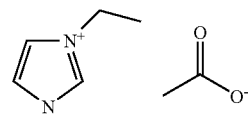<br>1 eq (36.5% strength in H₂O)<br><br>1 eq (40% strength in H₂O)<br><br>1 eq | 1 eq of glyoxal soution and 1 eq of formalin and 1 eq of glacial acetic acid are placed in a reaction vessel (slightly exothermic reaction), homogeneous. 2 eq of tert-butylamine added dropwise at <30° C. (exothermic reaction, cooling in an ice bath). The turbid solution admixed with toluene, stirred overnight at RT. Mixture evaporated, R1 (dark brown viscous oil having a solids content) Cryistallization by means of toluene, EE, butanol, isopropanol | 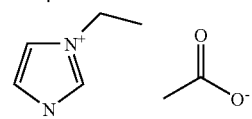 |

TABLE 1-continued with examples 2 to 11

| Example No. | Starting material 1 | Further starting materials | Work-up and procedure | Product (determined by (1H NMR)) |
|---|---|---|---|---|
| 11 | benzylamine (PhCH2NH2), 2 eq | formaldehyde (H-CHO), 1 eq (36.5% strength in H2O); glyoxal (OHC-CHO), 1 eq (40% strength in H2O); acetic acid (CH3COOH), 1 eq | 1 eq of glyoxal solution and 1 eq of formalin and 1 eq of glacial acetic acid are placed in a reaction vessel (slightly exothermic reaction), homogeneous. 2 eq of benzylamine added dropwise at <30° C. (exothermic, cooling in an ice bath, solid precipitates). Toluene added, the mixture stirred at RT over the weekend. Mixture (2 phases) evaporated (dark brown oil, not homogeneous) Product distributed in toluene and H2O. H2O phase evaporated on a rotary evaporator (dark brown oil). Toluene phase evaporated (dark brown oil). | 1,3-dibenzylimidazolium acetate |

Abbreviations:
1 eq, 2 eq corresponds to 1 mol, 2 mol
MMIM: 1,3-dimethylimidazolium
EEIM: 1,3-diethylimidazolium
EMIM: 1-ethyl-3-methylimidazolium Example 12

Continuous Preparation of 1,3-diethylimidazolium Acetate (EEIM Acetate)

Molar ratio of the starting materials glyoxal (Gly), formaldehyde (FA), acetic acid or glacial acetic acid (AA), ethylamine (EA):
Gly:FA:AA:EA=1:1:1:2

The carbonyl components (Gly, FA and AA) were mixed beforehand and introduced continuously as feed stream 1.

Feed Stream 1:
8 mol of glyoxal (40% strength), 8 mol of formaldehyde (40% strength), 8 mol of glacial acetic acid,
total: 2249 g Feed Stream 2:
16 mol of ethylamine (70% strength); 1029 g Feed stream 1 was fed at 8.73 ml/hour and feed stream 2 was fed at 5.97 ml/hour into the first stirred vessel of a cascade of two stirred vessels.

The experiment was carried out at various temperatures:

| Experiment | Residence time minutes | Temperature ° C. | Yield of EEIM (1 H-NMR), mol % |
|---|---|---|---|
| 12a | 22 | 24 | 85 |
| 12b | 30 | 40 | 96 |
| 12c | 30 | 60 | 79 |

The invention claimed is:

1. A process for preparing a 1,3-disubstituted imidazolium salt represented by the following formula I:

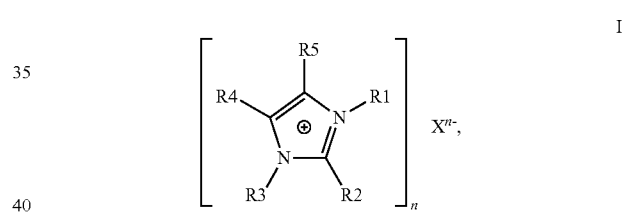

wherein
each of R1 and R3 is, independently of one another, a C1-C10-alkyl group,
each of R2, R4 and R5 is, independently of one another, an H atom or a C1-C10-alkyl group,
X is the anion of a hydrogen acid having a $pK_a$ of at least 2, measured at 25° C., 1 bar in water or dimethyl sulfoxide, and
n is 1, 2 or 3,
the process comprising:
reacting an α-dicarbonyl compound, an aldehyde, an amine and the hydrogen acid of the anion X⁻ with one another in a single stage, thereby obtaining a reaction product,
wherein the reacting is carried out in water, a solvent which is miscible with water or a mixture thereof, and the solubility of the imidazolium salt is at least 50 grams per 1 liter of water at 1 bar and 21° C.,
wherein X is selected from the group consisting of a benzoate anion, an anion of a C1-C20 alkanecarboxylic acid, and a mixture thereof,
wherein the reaction mixture does not comprise a hydrophobic organic solvent which is immiscible with water, and wherein removal of said water or solvent after the reaction is carried out without using a hydrophobic organic solvent which is immiscible with water.

2. The process according to claim 1, wherein R1 and R3 are the same and the imidazolium salt is a symmetrical, disubstituted imidazolium salt.

3. The process according to claim 1, wherein the imidazolium salt is a mixture of imidazolium salts of the formula I.

4. The process according to claim 1, wherein n is 1.

5. The process according to claim 1, wherein the $pK_a$ of the hydrogen acid of the anion X is from 3 to 8.

6. A process for preparing a 1,3-disubstituted imidazolium salt represented by the following formula I:

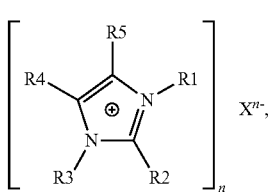

wherein
each of R1 and R3 is, independently of one another, a C1-C10-alkyl group,
each of R2, R4 and R5 is, independently of one another, an H atom or a C1-C10-alkyl group,
X is the anion of a hydrogen acid having a $pK_a$ of at least 2, measured at 25° C., 1 bar in water or dimethyl sulfoxide, and
n is 1, 2 or 3,
the process comprising:
reacting an α-dicarbonyl compound, an aldehyde, an amine and the hydrogen acid of the anion X⁻ with one another in a single stage, thereby obtaining a reaction product,
wherein the reacting is carried out in water, a solvent which is miscible with water or a mixture thereof, and the solubility of the imidazolium salt is at least 50 grams per 1 liter of water at 1 bar and 21° C.,
wherein X is the anion of a compound having at least one carboxylate group.

7. The process according to claim 6, wherein X is the acetate anion.

8. The process according to claim 1, wherein the α-dicarbonyl compound is a compound represented by the following formula II

  R4—CO—CO—R5    II, wherein R4 and R5 are as defined in claim 1.

9. The process according to claim 8, wherein the α-dicarbonyl compound is glyoxal.

10. The process according to claim 1, wherein the aldehyde is an aldehyde of the formula R2-CHO, where R2 is as defined in claim 1.

11. The process according to claim 1, wherein the amine is an amine of the formula R1-NH2 or a mixture of amines having different radicals R1.

12. The process according to claim 1, wherein the hydrogen acid of the anion X is a C1-C20 alkanecarboxylic acid.

13. The process according to claim 1, wherein the hydrogen acid of the anion X is acetic acid.

14. The process according to claim 1, wherein the reaction is carried out in water.

15. The process according to claim 1, wherein the water or the water-comprising solvent mixture is distilled off without use of an entrainer after the reaction.

16. The process according to claim 1, wherein the process is carried out continuously.

17. The process according to claim 1 which is carried out continuously and in which the α-dicarbonyl compound, the aldehyde and, optionally, the hydrogen acid of the anion X, are mixed beforehand and fed together as one feed stream into the reaction vessel.

18. The process according to claim 1, wherein the reaction product obtained is treated with an oxidant.

19. The process according to claim 18, wherein the oxidant is hydrogen peroxide.

20. A process for preparing a 1,3-disubstituted imidazolium salt represented by the following formula I:

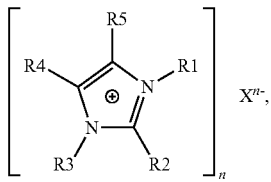

wherein
each of R1 and R3 is, independently of one another, an organic radical having from 1 to 20 carbon atoms,
each of R2, R4 and R5 is, independently of one another, an H atom or an organic radical having from 1 to 20 carbon atoms,
X is the anion of a hydrogen acid having a $pK_a$ of at least 2, measured at 25° C., 1 bar in water or dimethyl sulfoxide, and
n is 1, 2 or 3,
the process comprising:
reacting an α-dicarbonyl compound, an aldehyde, an amine, and the hydrogen acid of the anion X⁻ in a reaction mixture with one another in a single stage, thereby obtaining a reaction product,
wherein the reacting is carried out in water, a solvent which is miscible with water or a mixture thereof, with the proviso that the reaction mixture does not comprise a hydrophobic organic solvent which is immiscible with water during and/or after the reaction.

21. The process of claim 1, which is a continuous process.

22. The process of claim 6, which is a continuous process.

23. The process of claim 20, which is a continuous process.

24. The process of claim 6, wherein the reaction mixture does not comprise a hydrophobic organic solvent which is immiscible with water, and wherein removal of said water or solvent after the reaction is carried out without using a hydrophobic organic solvent which is immiscible with water.

25. The process of claim 20, wherein removal of said water or solvent after the reaction is carried out without using a hydrophobic organic solvent which is immiscible with water.

* * * * *